(12) United States Patent
Kumano et al.

(10) Patent No.: US 7,626,057 B2
(45) Date of Patent: Dec. 1, 2009

(54) PRODUCTION OF XYLYLENEDIAMINES

(75) Inventors: Tatsuyuki Kumano, Okayama (JP); Ryusuke Shigematsu, Okayama (JP); Kinji Kato, Okayama (JP); Kenji Nakaya, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/768,949

(22) Filed: Jun. 27, 2007

(65) Prior Publication Data
US 2008/0009654 A1 Jan. 10, 2008

(30) Foreign Application Priority Data
Jun. 29, 2006 (JP) .............................. 2006-179523

(51) Int. Cl.
*C07C 209/00* (2006.01)
(52) U.S. Cl. ....................... 564/415; 564/385
(58) Field of Classification Search .................. 564/415, 564/385
See application file for complete search history.

(56) References Cited

U.S. PATENT DOCUMENTS

| 3,803,204 A | 4/1974 | Grasselli |
| 2005/0004399 A1 * | 1/2005 | Amakawa et al. ........... 564/415 |

FOREIGN PATENT DOCUMENTS

| EP | 1449825 | 8/2004 |
| GB | 852972 | 11/1960 |
| GB | 1143390 | 2/1969 |
| JP | 43-13141 | 2/1974 |
| JP | 49-45860 | 5/1974 |
| JP | 53-020969 | 2/1978 |
| JP | 56-002941 | 1/1981 |
| JP | 63-190646 | 8/1988 |
| JP | 01-275551 | 11/1989 |
| JP | 05-170724 | 7/1993 |
| JP | 09-071561 | 3/1997 |
| JP | 2002-105035 | 4/2002 |
| JP | 2003-026639 | 1/2003 |
| WO | WO 2005/026098 A1 | 3/2005 |

OTHER PUBLICATIONS

Extended European Search Report for Application No. EP 07 11 1009, dated Sep. 27, 2007.

* cited by examiner

*Primary Examiner*—Daniel M Sullivan
*Assistant Examiner*—Sudhakar Katakam
(74) *Attorney, Agent, or Firm*—Antonelli, Terry, Stout & Kraus, LLP.

(57) ABSTRACT

A method of producing xylylenediamine by a two-stage hydrogenation of a starting phthalonitrile in a solvent. The main steps of the method are a hydrogenation step 1 and a hydrogenation step 2. In the hydrogenation step 1, a solution of the starting phthalonitrile in the solvent containing liquid ammonia is fed to an inlet of a first reaction zone and the hydrogenation is carried out in the first reaction zone in the presence of a heterogeneous catalyst, to hydrogenate nitrile groups in the starting phthalonitrile to aminomethyl groups. A part of the hydrogenation product solution from the first reaction zone is circulated to the inlet of the first reaction zone and the rest is introduced into the hydrogenation step 2 where further undergoes the hydrogenation.

8 Claims, 1 Drawing Sheet

PRODUCTION OF XYLYLENEDIAMINES

BACKGROUND OF THE INVENTION

1. Field of the Invention

The present invention relates to the production of xylylenediamines by the hydrogenation of phthalonitriles. Xylylenediamines are useful compounds as the raw materials for polyamide resins, curing agents, etc. and as the intermediates for isocyanate resins, etc.

2. Description of the Prior Art

The production of xylylenediamines by the hydrogenation of phthalonitrile in the presence of a heterogeneous catalyst in a continuous flow reactor has been well known. For example, a liquid-phase catalytic hydrogenation of phthalonitriles in the presence of a nickel-copper-molybdenum-containing catalyst is disclosed in JP 53-20969A. The hydrogenation is carried out using a fixed-bed continuous flow reactor in the working examples of JP 53-20969B. In another method, phthalonitriles obtained by the ammoxidation of xylylene are collected in an organic solvent, and then, after adding liquid ammonia without separating phthalonitriles, the collected phthalonitriles are continuously hydrogenated into corresponding xylylenediamines in a trickle bed reactor packed with a nickel and/or cobalt-containing catalyst (JP 2002-105035A). In still another method, isophthalonitrile obtained by the ammoxidation of m-xylylene is collected in an organic solvent, and then, the isophthalonitrile separated by distillation is continuously hydrogenated into corresponding m-xylylenediamine in a mixed solvent of liquid ammonia and hydrocarbon solvent in a trickle bed reactor packed with a nickel and/or cobalt-containing catalyst (JP 2003-26639A).

In another known method, phthalonitriles are hydrogenated to xylylenediamines in the presence of a heterogeneous catalyst using a continuous flow reactor while circulating a part of the reaction product solution from the continuous flow reactor to the inlet of the reactor (hereinafter referred to as "circulation method"). In GB 852972, it is taught that the circulation of the hydrogenation product solution as the solvent is advantageous in the hydrogenation of phthalonitriles to xylylenediamines in the presence of a cobalt-containing catalyst, and a production of m-xylylenediamine in the presence of a cobalt-manganese-containing catalyst using a fixed-bed continuous flow reactor is proposed in which the hydrogenation product solution is reused as a part of the solvent. The hydrogenation of nitrites to amines in the presence of a cobalt-containing catalyst is known, and GB 1143890 discloses the production of m-xylylenediamine by the circulation method in the presence of a cobalt-manganese-containing catalyst. In still another known method of producing xylylenediamines by the hydrogenation of phthalonitriles in liquid ammonia in the presence of a heterogeneous catalyst, molten phthalonitriles are dissolved in a hydrogenation product solution circulated as a part of the solvent and then fed to a fixed-bed continuous flow reactor for hydrogenation. It is taught that the selectivity is enhanced and the amount of liquid ammonia used can be reduced by the circulation of the hydrogenation product solution (WO 2005/026098).

It has been found, however, that the reaction intermediate such as cyanobenzylamines is likely to remain unchanged in the circulation method because of a reduced reaction rate. Cyanobenzylamines are required to be removed by separation, because it impairs the properties of resins, etc. However, it is difficult to separate cyanobenzylamines from xylylenediamines because of a small difference in their boiling points. The removal of cyanobenzylamines by amidation is disclosed in JP 56-2941A. However, the disclosed method requires a complicated apparatus and reduces the yield of xylylenediamines from phthalonitriles.

To solve the above problems, the hydrogenation should be completed as much as possible. However, a larger reactor and an increased amount of catalyst should be required for the completion of hydrogenation, making the process industrially disadvantageous.

SUMMARY OF THE INVENTION

An object of the present invention is to solve the problems in prior art and provide a circulation method for producing xylylenediamines by the hydrogenation of phthalonitriles using a simple apparatus with low costs.

As a result of extensive research, the inventors have found that the above object is achieved by a two-stage hydrogenation of a starting phthalonitrile, each stage being carried out under specific conditions.

Thus, the present invention relates to a method of producing xylylenediamine by a two-stage hydrogenation of a starting phthalonitrile in a solvent, which includes (1) a hydrogenation step 1 in which a 1 to 20% by weight solution of the starting phthalonitrile in the solvent containing liquid ammonia is fed to an inlet of a first reaction zone and the hydrogenation is carried out in the first reaction zone in the presence of a heterogeneous catalyst so as to convert 60 to 98% of total nitrile groups in the starting phthalonitrile to aminomethyl groups, thereby obtaining a first hydrogenation product solution, (2) a hydrogenation step 2 in which the first hydrogenation product solution undergoes the hydrogenation in a second reaction zone in the presence of a heterogeneous catalyst, thereby obtaining a second hydrogenation product solution in which a content of cyanobenzylamine is 0.2% by weight or less of xylylenediamine, and (3) a step in which the second hydrogenation product solution is distilled to remove the solvent and a crude product thus obtained is distilled, thereby obtaining a purified xylylenediamine, provided that 30 to 90% by weight of the first hydrogenation product solution discharged from the first reaction zone is circulated to the inlet of the first reaction zone and a rest thereof is introduced to the second reaction zone.

DETAILED DESCRIPTION OF THE INVENTION

Figure 1:
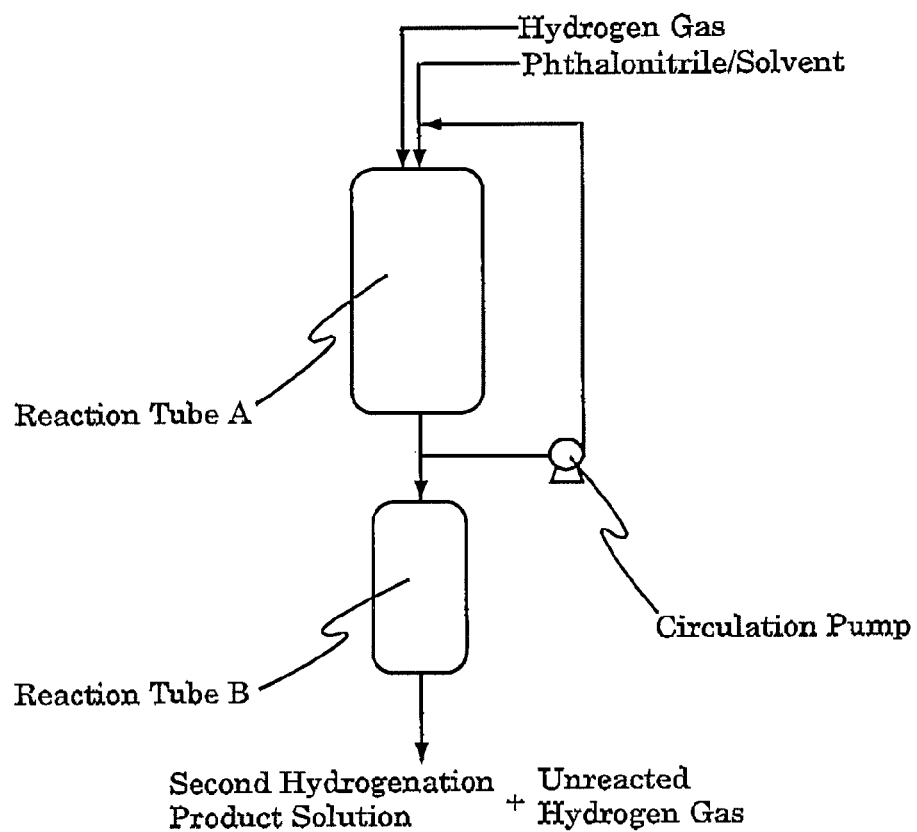
FIG. 1 is a schematic illustration of an apparatus used in the examples.

Xylylenediamine includes three isomers: o-xylylenediamine, m-xylylenediamine and p-xylylenediamine. The starting phthalonitrile includes orthophthalonitrile, isophthalonitrile and terephthalonitrile. The method of the present invention is preferably applicable to the production of m-xylylenediamine by the hydrogenation of isophthalonitrile.

Phthalonitrile is produced by the ammoxidation of an alkylbenzene such as xylene, the reaction between a dichlorobenzene and hydrogen cyanide, the reaction between phthalic acid and ammonia, etc., with the ammoxidation of an alkylbenzene being mainly employed in the industrial production. For example, the ammoxidation of xylene is conducted by a known method in the presence of a known catalyst (JP 49-45860B, JP 49-13141A, JP 63-190646A, JP 5-170724A, JP 1-275551A, JP 5-170724A, and JP 9-71561A).

The molten starting phthalonitrile produced by the above methods or the starting phthalonitrile converted into solid is dissolved in a solvent containing liquid ammonia in a mixing vessel. The resultant solution is fed to the inlet of the first reaction zone of the hydrogenation step 1. The concentration of phthalonitrile in the solution is preferably 1 to 20% by weight and more preferably 5 to 15% by weight. Within the above range, a large quantity of energy is not required for the recovery of solvent and the selectivity of the hydrogenation is good.

In addition to liquid ammonia, organic solvents stable under the conditions of the hydrogenation are usable in combination. Examples of the organic solvent include aromatic hydrocarbons such as toluene, xylene and trimethylbenzene; ethers such as tetrahydrofuran and dioxane; alcohols such as methanol, ethanol and propanol; and aromatic monoamines such as benzylamine and methylbenzylamine, with aromatic hydrocarbons being particularly preferred. The content of liquid ammonia in the mixed solvent is preferably 50% by weight or more.

Hydrogen gas to be supplied to the inlet of the first reaction zone of the hydrogenation step 1 may contain impurities such as methane and nitrogen which are inert to the hydrogenation. An excessively high content of impurities requires a high reaction pressure so as to assure a hydrogen partial pressure enough to conduct the hydrogenation, to make the process industrially disadvantageous. Therefore, the concentration of hydrogen is preferably 50 mol % or more.

In the hydrogenation step 1, the hydrogenation is conducted in a circulation manner in the presence of a heterogeneous catalyst, preferably in the form of a fixed bed. The heterogeneous catalyst is selected from known catalysts such as supported metal catalysts, non-supported metal catalysts, Raney catalysts, and noble metal catalysts, with supported metal catalysts in the form of granules and pellets being preferred. The metal is preferably nickel, cobalt, or palladium. The content of metal in the supported metal catalysts is preferably 10 to 95% by weight, more preferably 20 to 80% by weight, and still more preferably 30 to 70% by weight. The carrier is preferably diatomaceous earth, silica, alumina, silica-alumina, magnesia, zirconia, titania or activated carbon. The amount of the heterogeneous catalyst to be used is preferably 1 to 100 times, more preferably 2 to 50 times and still more preferably 5 to 20 times the amount of the starting phthalonitrile supplied to the hydrogenation step 1 per one hour, each being based on the weight.

The reaction temperature in the hydrogenation step 1 is preferably 20 to 200° C. and more preferably 30 to 180° C. The reaction pressure is preferably 1 to 30 MPa and more preferably 3 to 20 MPa.

In the hydrogenation step 1, 60 to 98 mol %, preferably 75 to 98 mol % and more preferably 85 to 98 mol % of the total nitrile groups in the starting phthalonitrile are hydrogenated into aminomethyl groups. If less than 60 mol %, the load of the subsequent second reaction zone is increased to reduce the selectivity of xylylenediamines in the hydrogenation step 2. To achieve a degree of hydrogenation higher than 98%, a large amount of catalyst is required to make the process industrially disadvantageous. The degree of hydrogenation of nitrile groups ($Y_1$ (mol %)) in the hydrogenation step 1 is determined from the following formula 1:

$$Y_1 = 100 \times (2B_1 + C_1)/2A \quad (1)$$

wherein $Y_1$ is the degree of hydrogenation of the total nitrile groups in the starting phthalonitrile to aminomethyl groups; A is the molar amount of the starting phthalonitrile supplied to the inlet of the hydrogenation step 1 per unit time; $B_1$ is the molar amount of xylylenediamine obtained at the outlet of the hydrogenation step 1 per unit time; and $C_1$ is the molar amount of cyanobenzylamine obtained at the outlet of the hydrogenation step 1 per unit time.

Apart of the hydrogenation product solution which is discharged from the outlet of the first reaction zone is returned to the inlet of the first reaction zone for circulation in an amount of preferably 30 to 90% by weight, more preferably 40 to 85% by weight and still more preferably 50 to 80% by weight each based on the amount of the hydrogenation product solution discharged from the outlet of the first reaction zone. If less than 30% by weight, the selectivity is low and the effect of circulation is not obtained. If more than 90% by weight, the apparatus for circulation becomes excessively large, to increase the apparatus costs. The circulated hydrogenation product solution is controlled for its temperature by a heat exchanger, etc. so as to regulate the reaction temperature.

The rest of the hydrogenation product solution is introduced into the hydrogenation step 2. In the hydrogenation step 2, the hydrogenation product solution is hydrogenated in the second reaction zone in a flow reaction manner to complete the hydrogenation. In the industrial production, the hydrogenation operations in the first reaction zone and the second reaction zone may be conducted in different reaction towers, or may be continuously conducted in a single reaction tower, with the latter operation being preferred because of low apparatus costs.

The hydrogenation in the hydrogenation step 2 is conducted in the presence of a heterogeneous catalyst, preferably in a fixed-bed manner. The heterogeneous catalyst is selected from known catalysts such as supported metal catalysts, non-supported metal catalysts, Raney catalysts, and noble metal catalysts, with supported metal catalysts in the form of granules and pellets being preferred. The metal is preferably nickel, cobalt, or palladium. The content of metal in the supported metal catalyst is preferably 10 to 95% by weight, more preferably 20 to 80% by weight, and still more preferably 30 to 70% by weight. The carrier is preferably diatomaceous earth, silica, alumina, silica-alumina, magnesia, zirconia, titania or activated carbon. The amount of the catalyst used in the hydrogenation step 2 is preferably 0.1 to 1 time and more preferably 0.3 to 1 time the weight of the catalyst used in the hydrogenation step 1.

The reaction temperature of the hydrogenation step 2 is preferably 20 to 200° C. and more preferably 30 to 180° C. The reaction temperature of the hydrogenation step 2 is preferably the same as or higher than that of the first reaction zone, more preferably 1 to 40° C. higher than that of the first reaction zone, because the amount of cyanobenzylamine is reduced to an intended level or lower. The reaction temperature can be effectively controlled by a heat exchanger, etc. disposed to the line for supplying the reaction product solution which interconnects the outlet of the hydrogenation step 1 and the inlet of the second reaction zone of the hydrogenation step 2.

The reaction pressure of the hydrogenation step 2 is preferably 1 to 30 MPa and more preferably 3 to 20 MPa. In the hydrogenation step 2, a fresh hydrogen having the same quality as that of hydrogen used in the hydrogenation step 1 may be supplied to the inlet of the second reaction zone. However, it is industrially advantageous to utilize the non-reacted hydrogen in the hydrogenation step 1.

In the hydrogenation step 2, the hydrogenation is continued until the amount of cyanobenzylamine in the second hydrogenation product solution is reduced preferably to 0.2% by weight or less and more preferably to 0.1% by weight or less of the weight of xylylenediamine. If cyanobenzylamine remains exceeding 0.2% by weight of xylylenediamine, it is difficult to obtain xylylenediamine with a sufficient quality.

After the hydrogenation step 2, a step for removing cyanobenzylamine from the obtained product may be provided, if necessary. For example, cyanobenzylamine is removed, but not limited to, by hydrating cyanobenzylamine to cyanobenzlamide which is relatively easily removed by distillation (step of removal by amidation) or by removing the solvent containing ammonia and then re-hydrogenating cyanobenzylamine to xylylenediamine (step of re-hydrogenation), with the step of re-hydrogenation being preferred because the yield of xylylenediamine based on the starting phthalonitrile is lowered in the step of removal by amidation. The reaction temperature in the step of re-hydrogenation is preferably 30 to 150° C. and more preferably 40 to 100° C. If 30° C. or more, an excessive reduction in the conversion of cyanobenzylamine is avoided. If 150° C. or less, xylylenediamine is prevented from being significantly subject to hydrogenation on its benzene ring and deamination and also prevented from being degraded by heating. The hydrogen partial pressure in the step of re-hydrogenation is preferably 0.1 to 10 MPa and more preferably 0.5 to 8 MPa. If 0.1 MPa or more, an excessive reduction in the conversion of cyanobenzylamine is avoided. If 10 MPa or less, xylylenediamine is prevented from being significantly subject to hydrogenation on its benzene ring and deamination.

In the method of the present invention, the starting phthalonitrile is hydrogenated in the hydrogenation step 1 and hydrogenation step 2. Thereafter, the solvent is distilled off and the obtained crude product is purified by distillation to obtain xylylenediamine. In the removal of the solvent, ammonia is first evaporated off, and then, the organic solvent is distilled off under reduced pressure or ordinary pressure. The obtained crude xylylenediamine is distilled under reduced pressure, preferably 1 to 30 kPa, to obtain a purified xylylenediamine.

The present invention will be described in more detail with reference to the examples. However, it should be noted that the scope of the present invention is not limited to the following examples.

Gas Chromatographic Analysis

The starting materials and sampled solutions were diluted with methanol, dioxane or tetrahydrofuran to prepare test solutions containing 1 to 5% by weight of the components other than the solvent. The test solutions were qualitatively and quantitatively analyzed by a gas chromatograph 6890 (Agilent) equipped with DB-1 column (Agilent (J & W)).

EXAMPLE 1

An experimental apparatus shown in FIG. 1, which was composed of a reaction tube A for the first reaction zone and a reaction tube B for the second reaction zone, was used. Each reaction tube was made of SUS and had an inner diameter of 25 mm. A nickel/diatomaceous earth catalyst with a column shape having a diameter of 3 mm and a length of 3 mm (nickel content: 50% by weight) was packed in each reaction tube in an amount of 120 mL for the reaction tube A and 60 mL for the reaction tube B. The catalyst was reduced for activation at 200° C. under hydrogen gas flow. After cooling, hydrogen gas was introduced under pressure into the reaction tubes A and B and a pipe connecting the reaction tubes. The pressure was kept constant at 8 MPa, and the catalyst layer temperature was kept at 75° C. in the reaction tube A and 80° C. in the reaction tube B under external heating.

Then, hydrogen gas was supplied from the inlet of the reaction tube A at a flow rate of 13 NL/h (NL: normal litter) and allowed to discharge from the reaction tube B. While keeping the flow of hydrogen gas, a starting solution containing 1 part by weight of the starting isophthalonitrile and 9 parts by weight of liquid ammonia was supplied from the inlet of the reaction tube A in a rate of 139 g/h. The hydrogenation was conducted continuously in the circulation manner while returning a part of the first hydrogenation product solution discharged from the reaction tube A to the inlet of the reaction tube A in a rate of 417 g/h (circulation rate: 75% by weight) by using a circulation pump. The first hydrogenation product solution discharged from the reaction tube A was sampled just before entering into the reaction tube B and analyzed by a gas chromatography. The conversion of the starting isophthalonitrile was 95.2 mol %, the selectivity of m-xylylenediamine was 85.4 mol %, and the selectivity of 3-cyanobenzylamine was 6.5 mol %. In addition, 84.4% of the total nitrile groups in the starting isophthalonitrile were hydrogenated to aminomethyl groups.

The rest of the first hydrogenation product solution from the outlet of the reaction tube A was introduced into the inlet of the reaction tube B in a rate of 139 g/h together with unreacted hydrogen gas from the outlet of the reaction tube A, to continuously conduct the hydrogenation. Then, the second hydrogenation product solution and unreacted hydrogen gas were discharged from the outlet of the reaction tube B. The discharged second hydrogenation product solution was sampled and analyzed by a gas chromatography. The amount of 3-cyanobenzylamine was 0.046% by weight on the basis of the weight of m-xylylenediamine. The conversion of isophthalonitrile was 99.9 mol % or more, the selectivity of m-xylylenediamine was 91.9 mol % and the selectivity of 3-cyanobenzylamine was 0.0438 mol %, each being the overall value throughout the hydrogenation step 1 and the hydrogenation step 2.

After evaporating off ammonia from the second hydrogenation product solution, the crude m-xylylenediamine was distilled under reduced pressure (125° C., 6 Torr). The purified product contained 99.95% by weight of m-xylylenediamine and 480 ppm by weight of 3-cyanobenzylamine when determined by a gas chromatography.

COMPARATIVE EXAMPLE 1

The hydrogenation of phthalonitrile was conducted by using an experimental apparatus composed of a single reaction tube (SUS, 25-mm inner diameter) in place of the apparatus shown in FIG. 1.

A nickel/diatomaceous earth catalyst with a column shape having a diameter of 3 mm and a length of 3 mm (nickel content: 50% by weight) was packed in the reaction tube in an amount of 180 mL. The catalyst was reduced for activation at 200° C. under hydrogen gas flow. After cooling, hydrogen gas was introduced under pressure into the reaction tube. The pressure was kept constant at 8 MPa, and the catalyst layer temperature was kept at 80° C. under external heating.

Then, hydrogen gas was supplied from the inlet of the reaction tube at a flow rate of 13 NL/h. While keeping the flow of hydrogen gas, a starting solution containing 1 part by weight of the starting isophthalonitrile and 9 parts by weight of liquid ammonia was supplied from the inlet of the reaction tube in a rate of 139 g/h, to conduct the hydrogenation continuously. Apart of the hydrogenation product solution discharged from the reaction tube was returned to the inlet of the reaction tube in a rate of 417 g/h (circulation rate: 75% by weight) by using a circulation pump. After hydrogenation, the hydrogenation product solution and unreacted hydrogen gas were discharged from the outlet of the reaction tube. The discharged hydrogenation product solution was sampled and analyzed by a gas chromatography. The degree of hydrogenation of nitrile groups to aminomethyl groups was 90.6% on the basis of the total nitrile groups in the starting isophthalonitrile. The conversion of isophthalonitrile was 99.9 mol % or more, the selectivity of m-xylylenediamine was 89.0 mol % and the selectivity of 3-cyanobenzylamine was 3.10 mol %.

EXAMPLE 2

An experimental apparatus shown in FIG. 1, which was composed of a reaction tube A for the first reaction zone and a reaction tube 13 for the second reaction zone, was used. Each reaction tube was made of SUS and had an inner diameter of 35 mm. A nickel/diatomaceous earth catalyst with a column shape having a diameter of 5 mm and a length of 5 mm (nickel content: 50% by weight) was packed in each reaction tube in an amount of 240 mL for the reaction tube A and 120 mL for the reaction tube B. The catalyst was reduced for activation at 200° C. under hydrogen gas flow. After cooling, hydrogen gas was introduced under pressure into the reaction tubes A and B and a pipe connecting the reaction tubes. The pressure was kept constant at 8 MPa, and the catalyst layer temperature was kept at 75° C. in the reaction tube A and 80° C. in the reaction tube B under external heating.

Then, hydrogen gas was supplied from the inlet of the reaction tube A at a flow rate of 24 NL/h and allowed to discharge from the reaction tube B. While keeping the flow of hydrogen gas, a starting solution containing 1 part by weight of the starting isophthalonitrile and 9 parts by weight of liquid ammonia was supplied from the inlet of the reaction tube A in a rate of 252 g/h. The hydrogenation was conducted continuously in the circulation manner while returning a part of the first hydrogenation product solution discharged from the reaction tube A to the inlet of the reaction tube A in a rate of 756 g/h (circulation rate: 75% by weight) by using a circulation pump. The first hydrogenation product solution discharged from the reaction tube A was sampled just before entering into the reaction tube B and analyzed by a gas chromatography. The conversion of the starting isophthalonitrile was 96.0 mol %, the selectivity of m-xylylenediamine was 86.0 mol %, and the selectivity of 3-cyanobenzylamine was 6.10 mol %. In addition, 85.5% of the total nitrile groups in the starting isophthalonitrile were hydrogenated to aminomethyl groups.

The rest of the first hydrogenation product solution from the outlet of the reaction tube A was introduced into the inlet of the reaction tube B in a rate of 252 g/h together with unreacted hydrogen gas from the outlet of the reaction tube A, to continuously conduct the hydrogenation. Then, the second hydrogenation product solution and unreacted hydrogen gas were discharged from the outlet of the reaction tube B. The discharged second hydrogenation product solution was sampled and analyzed by a gas chromatography. The amount of 3-cyanobenzylamine was 0.055% by weight on the basis of the weight of m-xylylenediamine. The conversion of isophthalonitrile was 99.9 mol % or more, the selectivity of m-xylylenediamine was 92.0 mol % and the selectivity of 3-cyanobenzylamine was 0.0522 mol %, each being the overall value throughout the hydrogenation step 1 and the hydrogenation step 2.

After evaporating off ammonia from the second hydrogenation product solution, the crude m-xylylenediamine was distilled under reduced pressure (125° C., 6 Torr). The purified product contained 99.94% by weight of m-xylylenediamine and 570 ppm by weight of 3-cyanobenzylamine when determined by a gas chromatography.

COMPARATIVE EXAMPLE 2

The hydrogenation of phthalonitrile was conducted by using an experimental apparatus composed of a single reaction tube (SUS, 35-mm inner diameter) in place of the apparatus shown in FIG. 1.

A nickel/diatomaceous earth catalyst with a column shape having a diameter of 5 mm and a length of 5 mm (nickel content: 50% by weight) was packed in the reaction tube in an amount of 720 mL. The catalyst was reduced for activation at 200° C. under hydrogen gas flow. After cooling, hydrogen gas was introduced under pressure into the reaction tube. The pressure was kept constant at 8 MPa, and the catalyst layer temperature was kept at 80° C. under external heating.

Then, hydrogen gas was supplied from the inlet of the reaction tube at a flow rate of 24 NL/h. While keeping the flow of hydrogen gas, a starting solution containing 1 part by weight of the starting isophthalonitrile and 9 parts by weight of liquid ammonia was supplied from the inlet of the reaction tube in a rate of 252 g/h, to conduct the hydrogenation continuously. Apart of the hydrogenation product solution discharged from the reaction tube was returned to the inlet of the reaction tube in a rate of 756 g/h (circulation rate: 75% by weight) by using a circulation pump. After hydrogenation, the hydrogenation product solution and unreacted hydrogen gas were discharged from the outlet of the reaction tube. The discharged hydrogenation product solution was sampled and analyzed by a gas chromatography. The degree of hydrogenation of nitrile groups to aminomethyl groups was 91.5% on the basis of the total nitrile groups in the starting isophthalonitrile. The conversion of isophthalonitrile was 99.9 mol % or more, the selectivity of m-xylylenediamine was 90.7 mol % and the selectivity of 3-cyanobenzylamine was 1.50 mol %.

EXAMPLES 3-5 AND COMPARATIVE EXAMPLE 3

An experimental apparatus shown in FIG. 1, which was composed of a reaction tube A for the first reaction zone and a reaction tube B for the second reaction zone, was used. Each reaction tube was made of SUS and had an inner diameter of 12 mm. A nickel/diatomaceous earth catalyst (nickel content: 50% by weight) was crushed to a uniform size (12 to 22 mesh), which was then packed in the reaction tubes A and B. The catalyst was reduced for activation at 200° C. under hydrogen gas flow. After cooling, hydrogen gas was introduced under pressure into the reaction tubes A and B and a pipe connecting the reaction tubes. The pressure was kept constant at 8 MPa, and the catalyst layer temperatures in the reaction tubes A and B were kept at given temperatures under external heating. The packed amount of the catalyst and the temperatures of the reaction tubes in each experiment are shown in Table 1.

Hydrogen gas was supplied from the inlet of the reaction tube A at a flow rate of 3.0 NL/h and allowed to discharge from the reaction tube B. While keeping the flow of hydrogen gas, a starting solution containing 1 part by weight of the starting isophthalonitrile and 9 parts by weight of liquid ammonia was continuously supplied from the inlet of the reaction tube A in a rate of 31.5 g/h. Apart of the first hydrogenation product solution discharged from the reaction tube A was returned to the inlet of the reaction tube A in a rate of 94.5 g/h (circulation rate: 75% by weight) by using a circulation pump. The rest of the first hydrogenation product solution was introduced into the reaction tube B together with unreacted hydrogen gas from the outlet of the reaction tube A, to continuously conduct the hydrogenation. The degree of hydrogenation of nitrile groups in the starting isophthalonitrile to aminomethyl groups in the hydrogenation step 1, the amount of 3-cyanobenzylamine based on the weight of m-xylylenediamine in the second hydrogenation product solution, and the overall conversion of isophthalonitrile and overall selectivities of the products throughout the hydrogenation steps 1 and 2, each determined by a gas chromatography, are shown in Table 1.

After evaporating off ammonia from the second hydrogenation product solution, the crude m-xylylenediamine was distilled under reduced pressure (125° C., 6 Torr). The results of the gas chromatographic analysis on the purified m-xylylenediamine are shown in Table 1.

TABLE 1

|  | Examples | | | Comparative |
|---|---|---|---|---|
|  | 3 | 4 | 5 | Example 3 |
| Amount of Catalyst (mL) | | | | |
| reaction tube A | 30 | 15 | 15 | 10 |
| reaction tube B | 15 | 15 | 15 | 15 |
| Temperature of Catalyst (° C.) | | | | |
| reaction tube A | 75 | 75 | 65 | 75 |
| reaction tube B | 80 | 80 | 80 | 80 |
| Degree of Hydrogenation*1 (mol %) | | | | |
| hydrogenation step 1 | 91.3 | 75.4 | 60.6 | 52.9 |
| Weight Ratio*2 (wt %) | 0.008 | 0.043 | 0.091 | 0.526 |
| Conversion*3 (mol %) | >99.9 | >99.9 | >99.9 | >99.9 |
| Selectivity*4 (mol %) | | | | |
| m-xylylenediamine | 96.2 | 94.4 | 95.0 | 89.7 |
| 3-cyanobenzylamine | 0.007 | 0.042 | 0.089 | 0.486 |
| Concentration (after distillation, wt %) | | | | |
| m-xylylenediamine | >99.99 | 99.96 | 99.91 | 99.46 |
| 3-cyanobenzylamine | 0.008 | 0.045 | 0.094 | 0.539 |

*1Degree of hydrogenation of nitrile groups in the starting isophthalonitrile to aminomethyl groups.
*2Weight ratio, 3-cyanobenzylamine/m-xylylenediamine, in second hydrogenation product solution.
*3Overall conversion of isophthalonitrile throughout hydrogenation step 1 and hydrogenation step 2.
*4Overall selectivity throughout hydrogenation step 1 and hydrogenation step 2.

EXAMPLES 6-7

An experimental apparatus shown in FIG. 1, which was composed of a reaction tube A for the first reaction zone and a reaction tube B for the second reaction zone, was used. Each reaction tube was made of SUS and had an inner diameter of 12 mm. A nickel/diatomaceous earth catalyst (nickel content: 50% by weight) was crushed to a uniform size (12 to 22 mesh), which was then packed in the reaction tubes A and B. The packed amount of the catalyst in each experiment is shown in Table 2. The catalyst was reduced for activation at 200° C. under hydrogen gas flow. After cooling, hydrogen gas was introduced under pressure into the reaction tubes A and B and a pipe connecting the reaction tubes. The pressure was kept constant at 8 MPa, and the catalyst layer temperature was kept at 75° C. in the reaction tube A and 80° C. in the reaction tube B under external heating.

Hydrogen gas was supplied from the inlet of the reaction tube A at a flow rate of 3.0 NL/h and allowed to discharge from the reaction tube B. While keeping the flow of hydrogen gas, a starting solution containing the starting isophthalonitrile and liquid ammonia in a given ratio was continuously supplied from the inlet of the reaction tube A in a rate of 315 g/h (Example 6) or 15.8 g/h (Example 7). Apart (75% by weight) of the first hydrogenation product solution discharged from the reaction tube A was returned to the inlet of the reaction tube A. The composition of the starting solution is shown in Table 2. The rest of the first hydrogenation product solution was introduced into the reaction tube B together with unreacted hydrogen gas from the outlet of the reaction tube A and the hydrogenation was conducted continuously. The degree of hydrogenation of nitrile groups in the starting isophthalonitrile to aminomethyl groups in the hydrogenation step 1, the amount of 3-cyanobenzylamine based on the weight of m-xylylenediamine in the second hydrogenation product solution, and the overall conversion of isophthalonitrile and overall selectivities of the products throughout the hydrogenation steps 1 and 2, each determined by a gas chromatography, are shown in Table 2.

After evaporating off ammonia from the second hydrogenation product solution, the crude m-xylylenediamine was distilled under reduced pressure (125° C., 6 Torr). The results of the gas chromatographic analysis on the purified m-xylylenediamine are shown in Table 2.

TABLE 2

|  | Examples | |
|---|---|---|
|  | 6 | 7 |
| Amount of Catalyst (mL) | | |
| reaction tube A | 30 | 15 |
| reaction tube B | 120 | 15 |
| Composition of Starting Solution (wt %) | | |
| isophthalonitrile | 1.0 | 20.0 |
| liquid ammonia | 99.0 | 80.0 |
| Degree of Hydrogenation*1 (mol %) | | |
| hydrogenation step 1 | 80.8 | 90.1 |
| Weight Ratio*2 (wt %) | 0.096 | 0.003 |
| Conversion*3 (mol %) | >99.9 | >99.9 |
| Selectivity*4 (mol %) | | |
| m-xylylenediamine | 97.8 | 93.1 |
| 3-cyanobenzylamine | 0.097 | 0.003 |
| Concentration (after distillation, wt %) | | |
| m-xylylenediamine | 99.90 | >99.99 |
| 3-cyanobenzylamine | 0.099 | 0.003 |

*1Degree of hydrogenation of nitrile groups in the starting isophthalonitrile to aminomethyl groups.
*2Weight ratio, 3-cyanobenzylamine/m-xylylenediamine, in second hydrogenation product solution.
*3Overall conversion of isophthalonitrile throughout hydrogenation step 1 and hydrogenation step 2.
*4Overall selectivity throughout hydrogenation step 1 and hydrogenation step 2.

EXAMPLE 8-9

An experimental apparatus shown in FIG. 1, which was composed of a reaction tube A for the first reaction zone and a reaction tube B for the second reaction zone, was used. Each reaction tube was made of SUS and had an inner diameter of 12 mm. A nickel/diatomaceous earth catalyst (nickel content:

50% by weight) was crushed to a uniform size (12 to 22 mesh), which was then packed in each reaction tube in an amount of 30 mL for the reaction tube A and 15 mL for the reaction tube B. The catalyst was reduced for activation at 200° C. under hydrogen gas flow. After cooling, hydrogen gas was introduced under pressure into the reaction tubes A and B and a pipe connecting the reaction tubes. The pressure was kept constant at 8 MPa, and the catalyst layer temperature was kept at 75° C. in the reaction tube A and 80° C. in the reaction tube B under external heating.

Hydrogen gas was supplied from the inlet of the reaction tube A at a flow rate of 3.0 NL/h and allowed to discharge from the reaction tube B. While keeping the flow of hydrogen gas, a starting solution containing 1 part by weight of the starting isophthalonitrile and 9 parts by weight of liquid ammonia was continuously supplied from the inlet of the reaction tube A in a rate of 31.5 g/h. A part of the first hydrogenation product solution discharged from the reaction tube A was returned to the inlet of the reaction tube A in a rate of 15.8 g/h (Example 8) or 284 g/h (Example 9). The rest of the first hydrogenation product solution was introduced into the reaction tube B together with unreacted hydrogen gas from the outlet of the reaction tube A, to continuously conduct the hydrogenation. The degree of hydrogenation of nitrile groups in the starting isophthalonitrile to aminomethyl groups in the hydrogenation step 1, the amount of 3-cyanobenzylamine based on the weight of m-xylylenediamine in the second hydrogenation product solution, and the overall conversion of isophthalonitrile and overall selectivities of the products throughout the hydrogenation steps 1 and 2, each determined by a gas chromatography, are shown in Table 3.

After evaporating off ammonia from the second hydrogenation product solution, the crude m-xylylenediamine was distilled under reduced pressure (125° C., 6 Torr). The results of the gas chromatographic analysis on the purified m-xylylenediamine are shown in Table 3.

TABLE 3

|  | Examples | |
| --- | --- | --- |
|  | 8 | 9 |
| Circulation Rate (wt %) | 33.4 | 90.0 |
| Degree of Hydrogenation*[1] (mol %) | | |
| hydrogenation step 1 | 90.5 | 86.2 |
| Weight Ratio*[2] (wt %) | 0.005 | 0.047 |
| Conversion*[3] (mol %) | >99.9 | >99.9 |
| Selectivity*[4] (mol %) | | |
| m-xylylenediamine | 93.6 | 97.5 |
| 3-cyanobenzylamine | 0.005 | 0.047 |
| Concentration (after distillation, wt %) | | |
| m-xylylenediamine | >99.99 | 99.95 |
| 3-cyanobenzylamine | 0.005 | 0.048 |

*[1]Degree of hydrogenation of nitrile groups in the starting isophthalonitrile to aminomethyl groups.
*[2]Weight ratio, 3-cyanobenzylamine/m-xylylenediamine, in second hydrogenation product solution.
*[3]Overall conversion of isophthalonitrile throughout hydrogenation step 1 and hydrogenation step 2.
*[4]Overall selectivity throughout hydrogenation step 1 and hydrogenation step 2.

EXAMPLE 10

The hydrogenation was conducted in the same manner as in Example 2 except for maintaining the catalyst layer in the reaction tube B at 90° C. by external heating. The second hydrogenation product solution and unreacted hydrogen gas were discharged from the outlet of the reaction tube B. The discharged second hydrogenation product solution was sampled and analyzed by a gas chromatography. The amount of 3-cyanobenzylamine was 0.021% by weight on the basis of the weight of m-xylylenediamine. The conversion of isophthalonitrile was 99.9 mol % or more, the selectivity of m-xylylenediamine was 92.1 mol % and the selectivity of 3-cyanobenzylamine was 0.0201 mol %, each being the overall value throughout the hydrogenation step 1 and the hydrogenation step 2.

After evaporating off ammonia from the second hydrogenation product solution, the crude m-xylylenediamine was distilled under reduced pressure (125° C., 6 Torr). The purified product contained 99.98% by weight of m-xylylenediamine and 220 ppm by weight of 3-cyanobenzylamine when determined by a gas chromatography.

EXAMPLE 11

The hydrogenation was conducted in the same manner as in Example 2 except for changing the starting solution to a mixture of 1 part by weight of the starting isophthalonitrile, 8 parts by weight of liquid ammonia and 1 part by weight of m-xylene. The first hydrogenation product solution discharged from the reaction tube A was sampled just before entering into the reaction tube B and analyzed by a gas chromatography. The conversion of the starting isophthalonitrile was 95.4 mol %, the selectivity of m-xylylenediamine was 84.5 mol %, and the selectivity of 3-cyanobenzylamine was 6.20 mol %. In addition, 83.6% of the total nitrile groups in the starting isophthalonitrile were hydrogenated to aminomethyl groups in the hydrogenation step 1.

The second hydrogenation product solution and unreacted hydrogen gas were discharged from the outlet of the reaction tube B. The discharged second hydrogenation product solution was sampled and analyzed by a gas chromatography. The amount of 3-cyanobenzylamine was 0.057% by weight on the basis of the weight of m-xylylenediamine. The conversion of isophthalonitrile was 99.9 mol % or more, the selectivity of m-xylylenediamine was 90.6 mol % and the selectivity of 3-cyanobenzylamine was 0.0530 mol %, each being the overall value throughout the hydrogenation step 1 and the hydrogenation step 2.

After evaporating off ammonia from the second hydrogenation product solution, the crude m-xylylenediamine was distilled under reduced pressure (125° C., 6 Torr). The purified product contained 99.94% by weight of m-xylylenediamine and 580 ppm by weight of 3-cyanobenzylamine when determined by a gas chromatography.

EXAMPLE 12

By removing ammonia by evaporation from the second hydrogenation product solution discharged from the outlet of the reaction tube B which was obtained in Example 2, a crude xylylenediamine containing 92.1% by weight of m-xylylenediamine and 520 ppm by weight of 3-cyanobenzylamine was obtained.

In a SUS reaction tube having an inner diameter of 35 mm, 50 mL of a nickel/diatomaceous earth catalyst with a column shape having a diameter of 5 mm and a length of 5 mm (nickel content: 50% by weight) was packed. The catalyst was reduced for activation at 200° C. under hydrogen gas flow. After cooling, hydrogen gas was introduced under pressure into the reaction tube. The pressure was kept constant at 4 MPa, and the catalyst layer temperature was kept at 100° C. under external heating.

Then, hydrogen gas was supplied from the inlet of the reaction tube at a flow rate of 1.1 NL/h. While keeping the flow of hydrogen gas, the above crude xylylenediamine was supplied from the inlet of the reaction tube in a rate of 25.2 g/h, to conduct the re-hydrogenation continuously. The hydrogenation product solution and unreacted hydrogen gas were discharged from the outlet of the reaction tube. The discharged hydrogenation product solution was sampled and analyzed by a gas chromatography. The concentration of m-xylylenediamine was 91.7% by weight and the concentration of 3-cyanobenzylamine was less than the detection limit of 30 ppm by weight.

After evaporating off liquid ammonia from the obtained hydrogenation product solution, the crude m-xylylenediamine was distilled under reduced pressure (125° C., 6 Torr). The concentration of m-xylylenediamine was 99.99% by weight and the concentration of 3-cyanobenzylamine was less than the detection limit of 30 ppm by weight.

As described above, in the method of the present invention, the amount of the solvent containing liquid ammonia to be used is reduced while keeping high yields even when using a simple apparatus, to reduce the quantity of energy required for removing the solvent. Therefore, the present invention provides a cost-effective method of producing xylylenediamines by the hydrogenation of phthalonitriles. Thus, the present invention is of a great industrial value.

What is claimed is:

1. A method of producing xylylenediamine by a two-stage hydrogenation of a starting phthalonitrile in a solvent, which comprises:
   (1) a hydrogenation step 1 in which a 1 to 20% by weight solution of the starting phthalonitrile in the solvent containing liquid ammonia is fed to an inlet of a first reaction zone and the hydrogenation is carried out in the first reaction zone in the presence of a heterogeneous catalyst so as to convert 60 to 98% of a total nitrile groups in the starting phthalonitrile to aminomethyl groups, thereby obtaining a first hydrogenation product solution,
   (2) a hydrogenation step 2 in which the first hydrogenation product solution undergoes the hydrogenation in a second reaction zone in the presence of a heterogeneous catalyst, thereby obtaining a second hydrogenation product solution in which a content of cyanobenzylamine is 0.2% by weight or less of xylylenediamine, and
   (3) a step in which the second hydrogenation product solution is distilled to remove the solvent and a crude product thus obtained is distilled, thereby obtaining a purified xylylenediamine,
   provided that 30 to 90% by weight of the first hydrogenation product solution discharged from the first reaction zone is circulated to the inlet of the first reaction zone and a rest thereof is introduced to the second reaction zone.

2. The method according to claim 1, wherein m-xylylenediamine is produced by the hydrogenation of isophthalonitrile.

3. The method according to claim 1, wherein the solvent comprises liquid ammonia and 1 to 50% by weight of an aromatic hydrocarbon.

4. The method according to claim 1, wherein the hydrogenation step 2 is conducted at temperature which is 1 to 40° C. higher than that of the hydrogenation step 1.

5. The method according to claim 1, wherein the hydrogenation step 1 and the hydrogenation step 2 are conducted in a single reaction tower.

6. The method according to claim 1, which further comprises a step of re-hydrogenating cyanobenzylamine in the second hydrogenation product solution after removing the solvent containing ammonia.

7. The method according to claim 1, wherein 40 to 85% by weight of the first hydrogenation product solution discharged from the first reaction zone is returned from the outlet of the first reaction zone to the first reaction zone.

8. The method according to claim 1, wherein 50 to 80% by weight of the first hydrogenation product solution discharged from the first reaction zone is returned from the outlet of the first reaction zone to the inlet of the first reaction zone.

* * * * *